United States Patent

Lander et al.

[11] Patent Number: 5,891,047
[45] Date of Patent: Apr. 6, 1999

[54] DETECTING ABNORMAL ACTIVATION OF HEART

[75] Inventors: Paul Lander, Lincoln, Mass.; Pedro Gomis, La Guaira, Venezuela

[73] Assignee: Cambridge Heart, Inc., Bedford, Mass.

[21] Appl. No.: 818,131

[22] Filed: Mar. 14, 1997

[51] Int. Cl.[6] .................................................. A61N 5/0472
[52] U.S. Cl. ............................................................. 600/516
[58] Field of Search .................................. 600/515–518, 600/520

[56] References Cited

U.S. PATENT DOCUMENTS

| | | | |
|---|---|---|---|
| 3,759,248 | 9/1973 | Valiquette | 600/516 |
| 4,082,087 | 4/1978 | Howson | 128/2.06 E |
| 4,084,583 | 4/1978 | Hjort | 128/2.06 R |
| 4,211,237 | 7/1980 | Nagel | 128/698 |
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,622,980 | 11/1986 | Kunig . | |
| 4,630,204 | 12/1986 | Mortara | 364/417 |
| 4,732,157 | 3/1988 | Kaplan et al. | 128/696 |
| 4,751,931 | 6/1988 | Briller et al. | 128/700 |
| 4,760,540 | 7/1988 | Yuen | 364/724 |
| 4,781,201 | 11/1988 | Wright et al. | 128/671 |
| 4,783,660 | 11/1988 | Pierce | 342/101 |
| 4,793,361 | 12/1988 | DuFault | 128/696 |
| 4,802,491 | 2/1989 | Cohen et al. | 128/702 |
| 4,807,173 | 2/1989 | Sommen et al. | 364/724.18 |
| 4,917,099 | 4/1990 | Stice | 128/696 |
| 4,974,598 | 12/1990 | John | 128/696 |
| 4,979,110 | 12/1990 | Albrecht et al. | 364/413.83 |
| 4,993,423 | 2/1991 | Stice | 128/696 |
| 5,010,888 | 4/1991 | Jadvar et al. | 128/696 |
| 5,020,540 | 6/1991 | Chamoun . | |
| 5,020,541 | 6/1991 | Marriott | 128/723 |
| 5,046,504 | 9/1991 | Albert et l. . | |
| 5,054,496 | 10/1991 | Wen et al. . | |
| 5,107,849 | 4/1992 | Bellin et al. | 128/696 |
| 5,109,862 | 5/1992 | Kelen et al. . | |
| 5,146,926 | 9/1992 | Cohen | 128/710 |
| 5,148,812 | 9/1992 | Verrier et al. | 128/704 |
| 5,188,116 | 2/1993 | Pommrehn et al. | 128/696 |
| 5,234,404 | 8/1993 | Tuttle et al. | 604/20 |
| 5,237,995 | 8/1993 | Cano | 128/640 |
| 5,265,617 | 11/1993 | Verrier et al. | 128/704 |
| 5,318,037 | 6/1994 | Evans et al. | 128/696 |
| 5,323,783 | 6/1994 | Henkin et al. | 128/703 |
| 5,341,811 | 8/1994 | Cano | 128/696 |
| 5,348,020 | 9/1994 | Hutson | 128/696 |
| 5,365,426 | 11/1994 | Siegel et al. | 600/515 |
| 5,377,687 | 1/1995 | Evans et al. | 128/700 |
| 5,419,337 | 5/1995 | Dempsey et al . | |
| 5,421,342 | 6/1995 | Mortara | 128/696 |
| 5,437,285 | 8/1995 | Verrier et al. | 128/702 |
| 5,469,857 | 11/1995 | Laurent et al. | 128/710 |
| 5,509,425 | 4/1996 | Feng | 600/515 |
| 5,520,191 | 5/1996 | Karlsson et al . | |
| 5,520,683 | 5/1996 | Subramaniam et al. | 606/32 |
| 5,560,370 | 10/1996 | Verrier et al. | 128/705 |
| 5,570,696 | 11/1996 | Arnold et al. | 128/707 |

OTHER PUBLICATIONS

R. Plonsey, "Laws governing current flow in the volume conductor" in The Theoretical Basis of Electrocardiography, C.V. Nelson and D.B. Geselowitz, Eds., Clarendon Press, Oxford pp. 165–174, 1996.

*Primary Examiner*—William E. Kamm
*Attorney, Agent, or Firm*—Fish & Richardson PC

[57] ABSTRACT

Abnormal cardiac activity in a patient may be detected by acquiring an electrocardiogram waveform associated with a first level of physiologic activity of the patient and an electrocardiogram waveform associated with a second, different level of physiologic activity of the patient. QRS complexes of the electrocardiogram waveforms are compared to identify an abnormal portion of the QRS complex of the electrocardiogram waveform associated with the second level of physiologic activity. The abnormal portion of the QRS complex is processed to detect abnormal physiologic activity.

48 Claims, 14 Drawing Sheets

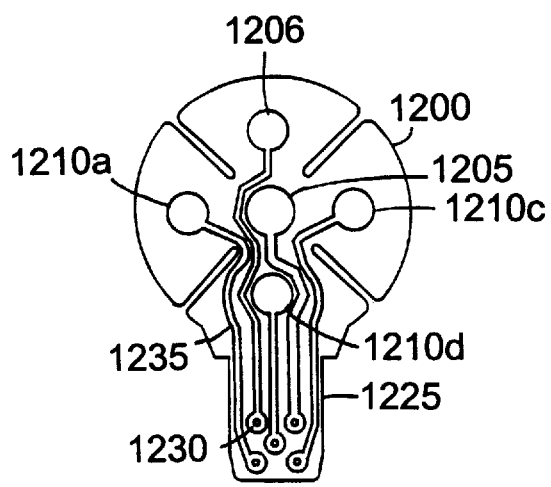
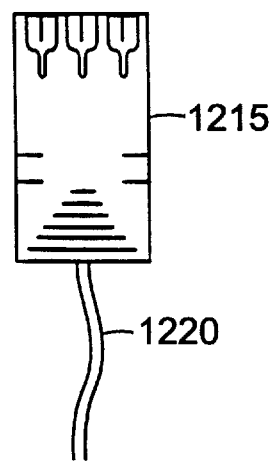
FIG. 11

DETECTING ABNORMAL ACTIVATION OF HEART

BACKGROUND

The invention relates to detecting abnormal activation of the heart.

Abnormal activation of the heart may be indicative of myocardial ischemia or myocardial infarction. Myocardial ischemia, which is also known as reduced myocardial blood flow, may be indicative of coronary artery disease. Myocardial ischemia may be provoked under clinical conditions by applying stress to a patient, and may be indicated by localized changes in heart function due to localized changes in myocardial blood flow. Accordingly, myocardial ischemia and related coronary artery disease may be diagnosed by measuring such localized changes in heart function.

Myocardial infarction is a more severe condition. Myocardial infarction may result in a complete loss of activation of areas of the heart. This results in loss of blood flow to areas of the heart.

Localized changes in heart finction resulting from myocardial ischemia or myocardial infarction may include electrical changes in the heart. Electrical activity of the heart generates an electrical potential on the body surface. At any given location on the body, this potential includes contributions from every region of the heart, with the contribution from a particular region being inversely proportional to the square of the distance from the region to the location on the body. Given the anatomy of the heart and chest, the potentials at most locations on the body surface effectively represent summed electrical activity from a large region of the heart.

The body surface electrocardiogram (ECG) is a measure of electrical activity of the heart. The ECG provides a measure of the potential difference between two points on the body surface as a continuous finction of time. The ECG is routinely measured using standard ECG electrodes.

SUMMARY

The invention features detecting abnormal activation of the heart as an indicator of myocardial ischemia or myocardial infarction. To this end, the invention includes measuring abnormal signals in the QRS complex of an electrocardiogram ("ECG") during periods of differing cardiac activity, such as may be associated with physiologic stress testing. The QRS complex of an ECG beat corresponds electrically to contraction of the ventricles of the heart.

Under conditions of normal myocardial blood flow, the net conduction vector of ventricular depolarization (i.e., the spread of a "wave" of electrical activation through the heart) is smooth and regular. In general, this results in a body surface ECG having a QRS complex with a regular pattern.

Myocardial insufficiency due to myocardial ischemia results when there is an obstruction in a coronary artery within the heart such that the heart demands more blood flow than the obstructed artery can provide. When this occurs, a small area in the immediate vicinity of the coronary obstruction receives inadequate blood flow. When the conduction vector (i.e., the electrical activation wave) arrives at this area, there may be an abrupt change in the net direction of the conduction vector. This direction change may result in a step change in the body surface potential. High pass filtering of the ECG may transform this step change into a notch or slur on the QRS complex. However, the notch or slur may be too small to be observable in the filtered ECG. In general, notches or slurs in the QRS complex may be referred to as abnormal intra-QRS potential ("AIQP") signals.

Thus, the area of myocardial insufficiency may disorder the depolarization. If this disordering is confined to a local region, it will result in a notch or slur in the filtered ECG. If the disordering becomes more global in nature, the shape of the QRS complex may be altered dramatically so as to result in a directly observable gross effect in the ECG.

Physiologic stress testing or other techniques for increasing the level of cardiac activity may be used to induce myocardial insufficiency associated with myocardial ischemia and coronary artery disease. In general, a physiologic stress test includes a rest stage in which an ECG having a normal QRS complex may be measured, and progressive stages of exercise during which changes may manifest in the QRS complex. These changes may result in notches and slurs that are difficult to detect because they are too small to be discerned visually from the standard ECG and because they are masked by noise.

During an acute myocardial infarction, ventricular tissue is progressively starved of blood, which eventually results in scarring of the tissue. While ischemic tissue may be partially conducting, scar tissue is non-conducting. As such, AIQP signal levels will increase during progressive myocardial ischemia associated with myocardial infarction, but may cease to increase in the presence of scarring. Accordingly, myocardial infarction may be diagnosed and monitored by measuring changes in AIQP signals over time.

Large-scale notches and slurs (>50 $\mu$V) have been associated with disruption in ventricular conduction due to scarring after myocardial infarction. However, small-scale changes in notches and slurs (<50 $\mu$V) in the presence of either myocardial ischemia or acute myocardial infarction have not been reported in the clinical literature. Ordinarily such signals are invisible in the standard ECG, as they are below the level of noise ordinarily experienced with exercise or other activity. They are also indistinguishably superimposed on the large, normal component of the QRS complex.

In one aspect, generally, the invention features detecting abnormal cardiac activity in a patient. Electrocardiogram waveforms associated with first and second levels of physiologic activity of the patient are acquired and QRS complexes of the electrocardiogram waveforms are compared to identify an abnormal portion of the QRS complex of the electrocardiogram waveform associated with the second level of physiologic activity. The abnormal portion of the QRS complex is then processed to detect abnormal cardiac activity.

Levels of physiologic activity may correspond to physiologic states induced by factors such as sleep, exercise, emotion, and patient motion or position. Characteristics of the heart rate may be indicative of the level of physiologic activity.

Embodiments of the invention may include one or more of the following features. The patient's heart may be stressed to produce the second level of physiologic activity. For example, a physiological stress test may be performed on the patient. In this instance, the first level of physiologic activity may be associated with a rest stage of the stress test, and the second level of physiologic activity may be associated with an increased exercise stage of the stress test.

Subensembles of beats in the electrocardiogram waveforms corresponding to the first and second levels of physiologic activity may be produced. Each subensemble of beats may be processed to produce a representative beat. QRS complexes of the representative beats may be processed to identify an abnormal portion of the QRS complex of the electrocardiogram waveform associated with the second level of physiologic activity. The representative beats may be produced by computing a measure of statistical central tendency from the subensemble of beats, such as by subensemble averaging or generation of median beats.

The QRS complexes may be compared by subtracting a QRS complex of the electrocardiogram associated with the first level of physiologic activity from a QRS complex of the electrocardiogram associated with the second level of physiologic activity. A model of the QRS complex of the electrocardiogram waveform associated with the first level of physiologic activity may be generated. The model then may be subtracted from the QRS complex of the electrocardiogram associated with the second level of physiologic activity.

Processing of the abnormal portion of the QRS complex may include determining a root-mean-square amplitude, energy, or duration of the abnormal portion. The processing also may include measuring timing or bandwidth of the abnormal portion relative to the QRS complex.

Electrocardiogram waveforms associated with other levels of physiologic activity of the patient also may be acquired. The QRS complexes of these waveforms may be compared to identify abnormal portions of the QRS complexes that then may be processed. Processing may include comparing the abnormal portions of the QRS complexes, measuring a parameter of each of the abnormal portions of the QRS complexes and comparing parameters associated with different QRS complexes, or identifying a trend in the abnormal portions for changing levels of physiologic activity.

Myocardial ischemia may be detected based on the abnormal portions of the QRS complexes. For example, a quantitative measure of a degree of myocardial ischemia may be determined. Similarly, a location of the myocardial ischemia may be determined based on the abnormal portion of the QRS complex.

In another aspect, generally, the invention features detecting myocardial infarction in a patient by continuously acquiring electrocardiogram waveforms associated with physiologic activity of the patient. QRS complexes of the electrocardiogram waveforms are compared to identify abnormal portions of the QRS complexes. Trends in the abnormal portions are identified to detect myocardial infarction.

In another aspect, generally, the invention features detecting abnormal cardiac activity in a patient after physiologically stressing the patient. An electrocardiogram waveform is acquired from the patient, and a model of a QRS complex of the electrocardiogram waveform is generated. The QRS complex of the electrocardiogram waveform is then compared to the model of the QRS complex to identify an abnormal portion of the QRS complex. The abnormal portion is then processed to detect abnormal cardiac activity.

Other features and advantages of the invention will be apparent from the following description, including the drawings, and from the claims.

BRIEF DESCRIPTION OF THE DRAWINGS

FIG. 11 is a top view of an electrode and a connector assembly of the system of FIG. 1.

DESCRIPTION

Figure 1:
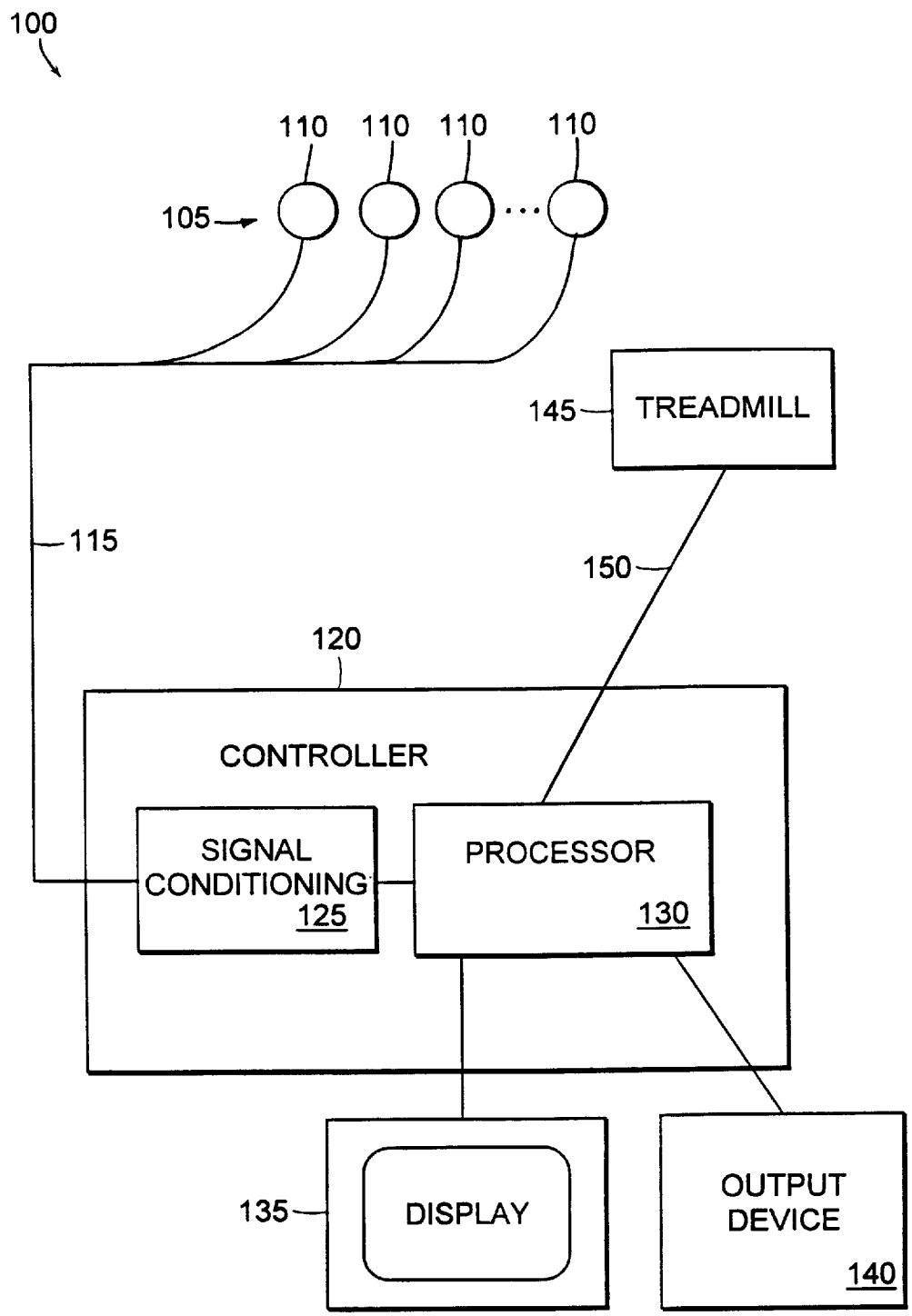
FIGS. 1 and 1A are block diagrams of ECG systems.
Figure 1A:
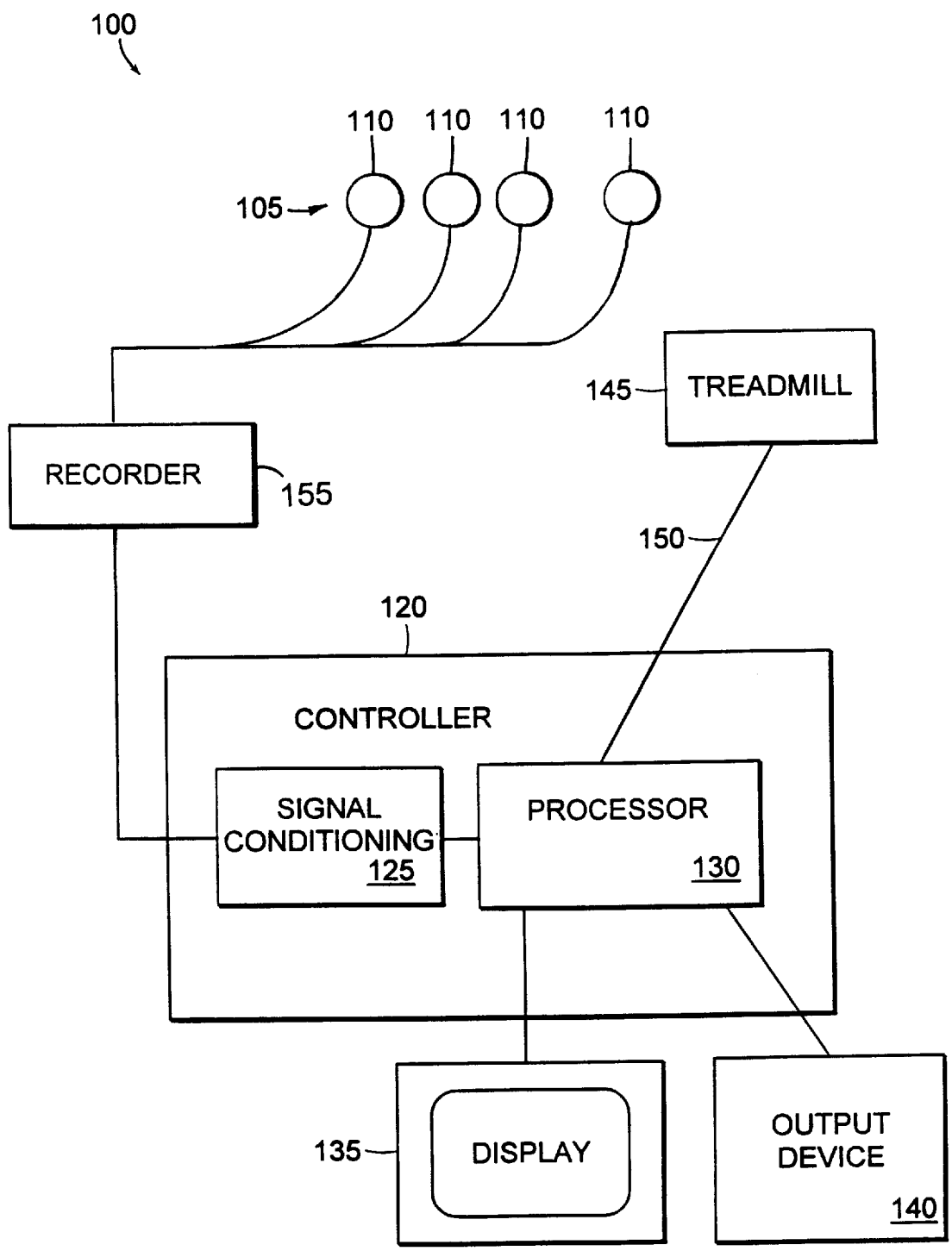

Referring to FIG. 1, a ECG system 100 that may be used to measure myocardial ischemia during physiologic stressing of a patient's heart includes a set 105 of electrodes 110. The electrodes may be standard ECG electrodes, or may be an array of electrodes applied to cover the anterior, lateral and posterior areas of the torso. The electrodes function separately from one another, but may be physically affixed together to form a flexible band or other arrangement. The system 100 further includes a set of leads 115 that connect the electrodes to a system controller 120. The controller includes signal conditioning circuitry 125 and a processor 130. The circuitry 125 receives analog signals from the leads 115 and provides conditioned digital signals to the processor 130. The processor 130 processes the conditioned signals to produce results that the processor then provides to a connected display 135 or to an output device 140, such as a printer. The processor may optionally control physiologic stress of the patient's heart by controlling an exercise device, such as a treadmill 145 having programmable slope and walking speed, through control signals supplied through a lead 150. Similarly, an optional recording device 155 (FIG. 1A) of an ambulatory system may be used to record signals from the leads for an extended period of time (e.g., 24 hours). The recording device 155 then is connected to the controller 120 to permit the controller 120 to process the recorded data.

Figure 2:
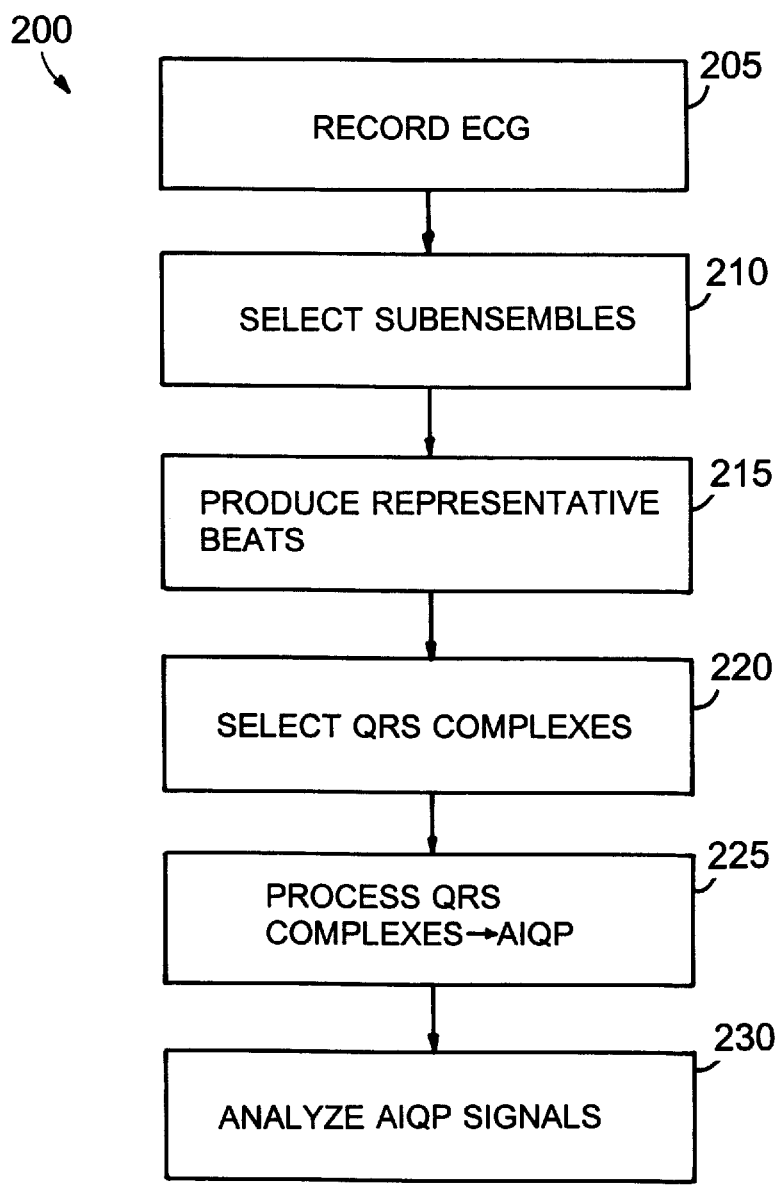
FIG. 2 is a flowchart of a procedure for detecting abnormal activation of the heart.

Referring to FIG. 2, the controller 120 processes ECG data according to a procedure 200. Initially, the controller 120 records a continuous ECG from the body surface using the electrodes 110 (step 205). The recorded ECG may correspond, for example, to a physiologic stress test that includes a rest period, stages of increasing stress, and a recovery period. This type of ECG may be analyzed to detect myocardial ischemia due to coronary artery disease. The recorded ECG also may correspond to a resting ECG recorded from a supine patient. A resting ECG may be recorded routinely or in an emergency room when an acute myocardial infarction is suspected. Similarly, the recorded ECG may be produced using a bedside monitor in a hospital. This may be done, for example, after a revascularization procedure, such as balloon angioplasty to open a previously occluded artery, in which case analysis of the ECG may identify reocclusion of the artery. The recorded ECG also may be produced using an ambulatory recorder to, for example, assess transient myocardial ischemia. Typically, an ECG produced using an ambulatory recorder will include twenty four hours or more of ECG data.

Next, the controller 120 selects subensembles of beats from the recorded ECG (step 210). The entire ECG recording is an ensemble of beats, and the controller 120 divides the ensemble into subensembles. Examples of subensembles may include: stages of a stress test; regular intervals (e.g., five to fifteen minute intervals in an emergency room); and periods of the day in, for example, ambulatory or hospital monitoring. Similarly, subensembles may be selected based on levels of physiologic activity associated with recorded data. By selecting subensembles, abnormal intra QRS potential ("AIQP") signals measured in each subensemble can be compared to each other. In addition, reference AIQP signals and signal levels can be designated, and time trends of AIQP signals changing in appearance or otherwise can be monitored and graphed.

Figure 3:
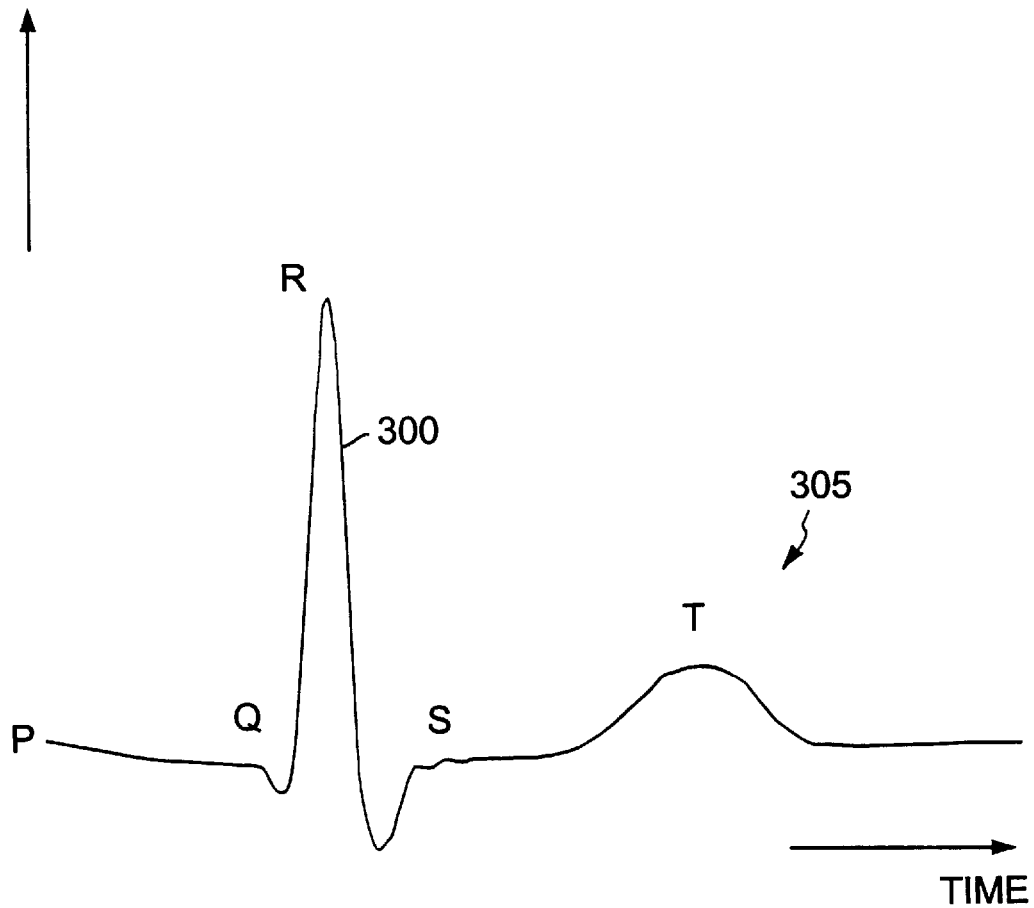
FIG. 3 is a schematic representation of an ECG waveform.

The controller 120 then produces a representative beat for each subensemble (step 215). In general, a representative beat is a low-noise beat obtained by combining a collection of beats that have been time-aligned. Time alignment may be performed at the QRS complex. See Lander et al., "Principles and Signal Processing Techniques of the High-Resolution Electrocardiogram", *Prog. Cardiovasc. Dis.* 35(3):169–188, 1992, which is incorporated by reference. Referring to FIG. 3, the QRS complex 300 of an ECG beat 305 corresponds to ventricular contraction. Techniques for combining beats to form a representative beat include median beat formation and subensemble averaging.

Finally, the controller 120 selects the QRS complexes of the representative beats to detect AIQP signals (step 225), and analyzes the AIQP signals to detect abnormal activation of the heart (step 230). During physiologic stress testing or under other conditions (e.g., ambulatory monitoring) in which the patient's cardiac level changes with time, the controller 120 may process the representative beats by subtracting a reference beat from a beat under consideration. For example, during physiologic stress testing, the QRS complex of the reference beat, $QRS_{ref}$, may be defined as the representative beat for the initial rest period of the stress test. As such, the AIQP signal, $AIQP_i$, in the QRS complex, $QRS_i$, of a subensemble i may be expressed as:

$$AIQP_i = QRS_i - QRS_{ref}$$

The AIQP signals for different stages of the stress test may be analyzed to automatically detect myocardial ischemia. For example, large changes in the magnitude of the AIQP signals as the level of exercise increases may be indicative of myocardial ischemia while small changes are not indicative of ischemia. Similarly, an AIQP signal having a value that exceeds a clinically determined threshold may indicate a risk of arrhythmia while an AIQP signal having a smaller value may be indicative of no such risk. A position within the QRS complex of the peak value of the AIQP signal may be indicative of the location of an occluded artery. For example, a peak in the first half of the QRS complex may be indicative of an occlusion in the left anterior descending artery while a peak in the second half may be indicative of an occlusion in the right coronary artery. A peak near the middle of the QRS complex may be indicative of an occlusion of the left circumflex artery. There may be considerable overlap between these regions. As an alternative to automatic processing, or in addition to such processing, the AIQP signals may be displayed on the display 135 to permit a clinician to determine whether the AIQP signals are indicative of myocardial ischemia and coronary artery disease.

The processing approach described above assumes that neither the AIQP signal nor significant noise is present in the reference beat. Another approach that is less sensitive to noise in the reference beat processes the representative beats by subtracting a model, $QRS_{ref}^M$, of the reference beat from a beat under consideration:

$$AIQP_i = QRS_i - QRS_{ref}^M.$$

Similarly, a model, $QRS_i^M$ may be generated for each beat under consideration and subtracted from the beat:

$$AIQP_i = QRS_i - QRS_1^M.$$

In general, the QRS complex can be modelled as the response of the cardiac system to an impulse stimulus at the atrioventricular node. Thus, the QRS complex may be expressed as the impulse response of a system represented by a linear difference equation:

$$y(n) = \sum_{k=0} g(k)\delta(n-k) = -\sum_{i=1} a_i y(n-i) + \sum_{j=0} b_j \delta(n-j)$$

where y(n) is a discrete-time signal of N samples, n equals 0, 1, 2, ..., N−1, δ(n) is the unit impulse, and the model is defined by the set of coefficients $a_i$ and $b_j$.

Figure 4:
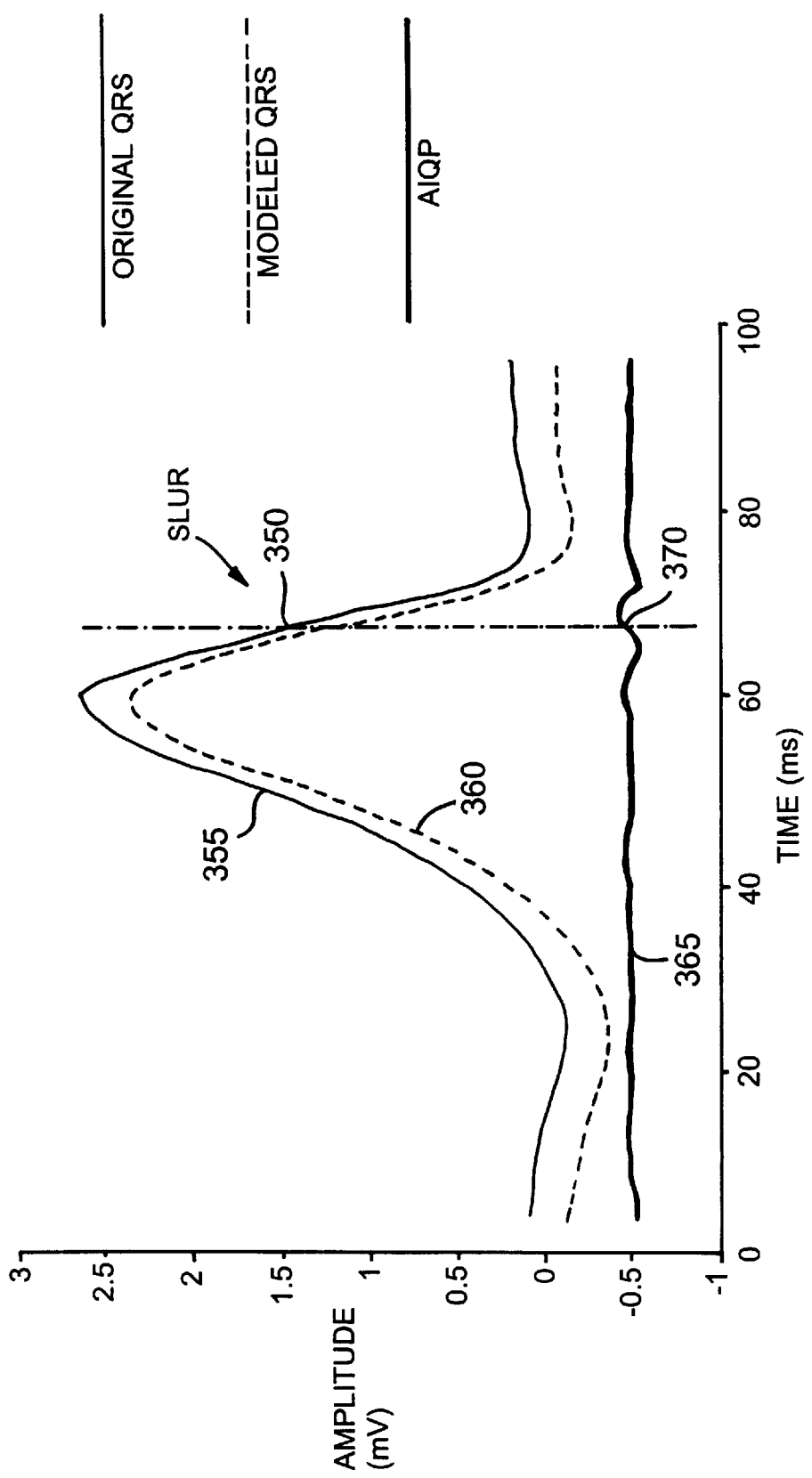
FIG. 4 is a graph of a relationship between QRS waveforms and an AIQP signal.

An AIQP signal may be defined as the difference between the original QRS complex and the modelled QRS complex. As shown in FIG. 4, a small slur 350 in the QRS complex 355 is not visibly apparent. However, subtracting a modeled QRS complex 360 from the original QRS complex results in an AIQP signal 365 having a readily-apparent peak 370 corresponding to the slur.

Figure 5:
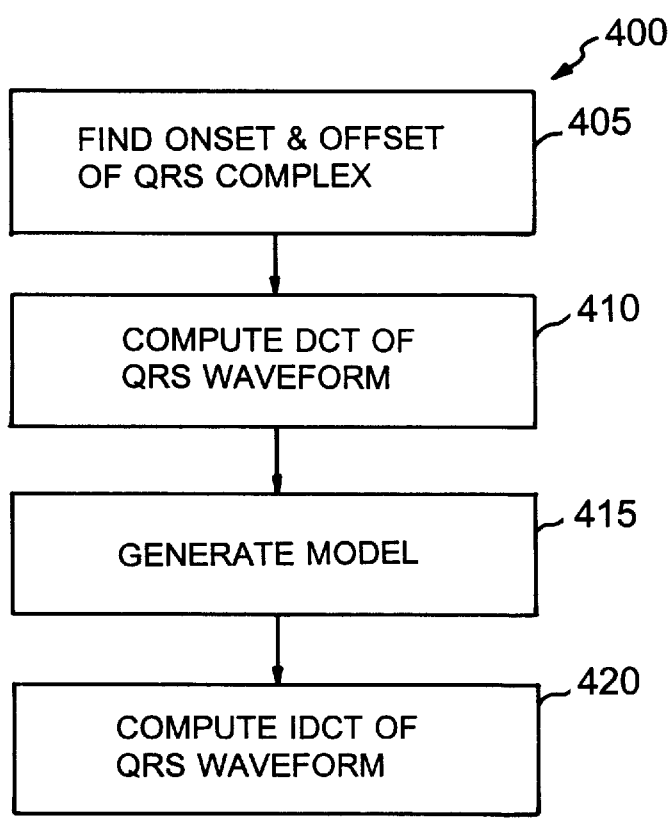
FIG. 5 is a flowchart of a procedure for modeling a QRS waveform.

The model of the reference beat may be produced according to the procedure 400 illustrated in FIG. 5. Initially, the onset and offset times of the QRS complex are found in the representative beat to produce a QRS waveform (step 405). The QRS onset time is computed from an absolute spatial velocity vector (ASVV). The ASVV is formed by simple differencing three ECG leads and combining them to form a vector magnitude. Any three leads that are approximately orthogonal to each other may be used. The QRS onset is defined by searching forward in time for the point in the PR interval (see FIG. 3) of the ECG waveform where the ASVV signal level increases abruptly, indicating the onset of the QRS complex.

The QRS offset time is determined from an ECG waveform filtered using a highpass filter having a cutoff frequency of 40 Hz. The filtered ST segment of the ECG waveform is searched backward in time until a significant increase in filtered ECG signal level is detected, indicating the end of the QRS complex.

Next, a Discrete Cosine Transform (DCT) is used to produce an energy-compacted form of the QRS waveform in the frequency domain (step 410). The DCT produces damped cosinusoidal waveshapes that are well suited for representation by rational transfer functions of relatively low order. For example, given a discrete signal x(n) of N samples, where n equals 0, 1, 2, ..., N−1, the DCT of x(n) may be expressed as:

$$X(k) = \sqrt{\frac{2}{N}} \, C_k \sum_{n=0}^{N-1} x(n) \cos\left[\frac{(2n+1)\pi}{2N}\right]$$

for k=0, 1, ..., N−1, and $$C_k = \begin{cases} 1/\sqrt{2} & k = 0 \\ 1 & k \neq 0 \end{cases}.$$

An impulse response model is then generated from the DCT using an iterative technique (step 415). The linear difference equation noted above may be expressed in the z-domain as:

$$G(z) = \frac{B(z)}{A(z)} = \frac{b_0 + b_1 z^{-1} + {}_+ b_{nb} z^{-nb}}{1 + a_1 z^{-1} + {}_+ a_{na} z^{-na}}$$

where $\delta(n)$ is the unit impulse, and na and nb are, respectively, the number of poles and zeros of the model.

Empirical analysis has shown that models having from approximately seven to twelve poles and zeroes (e.g., na equals ten and nb equals ten) provide good results in testing ECGs. Models having smaller numbers of poles and zeroes (e.g., na equals four and nb equals four) may not provide sufficient resolution. Similarly, models having larger numbers of poles and zeroes (e.g., na equals seventeen and nb equals seventeen) tend to incorporate noise and AIQP signals into the model.

Figure 6:
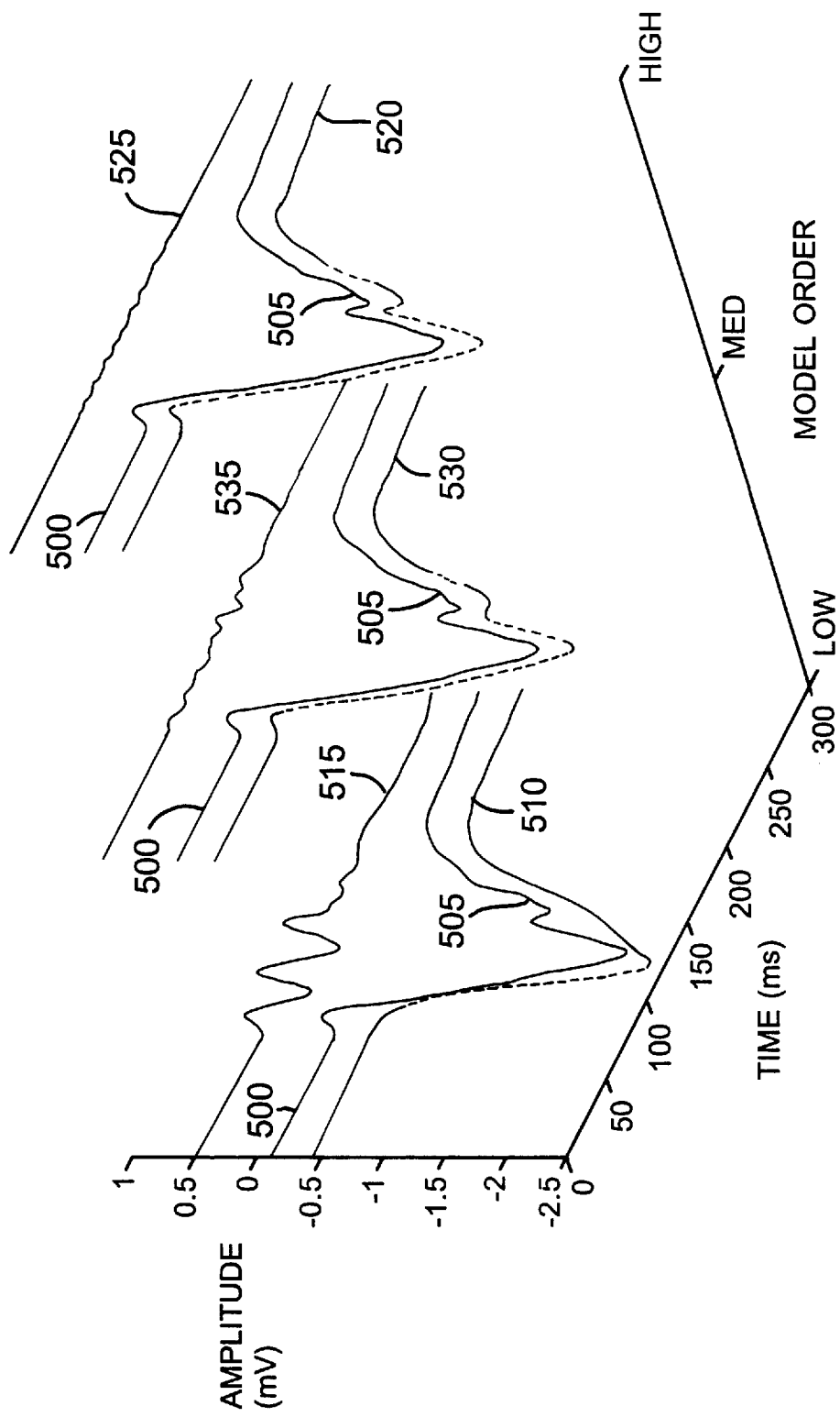
FIG. 6 is a graph of relationships between QRS waveforms and AIQP signals for different models.

For example, as shown in FIG. 6, three models for a QRS waveform 500 having a distinctive notch and slur 505 in the second half of the QRS waveform produce significantly different results. A low order model 510 (na=4, nb=4) produces a residual signal 515 (the difference between the modelled waveform 510 and the original waveform 500) that extracts the notch and slur effectively but has a poor overall fit to the whole QRS waveform. This results in spurious residual signals, particularly at the onset and peak of the QRS waveform. A high order model 520 (na=17, nb=17) accurately models both the normal and abnormal components of the QRS, so that the residual signal 515 is featureless. An intermediate order model 530 (na=10, nb=10) represents a compromise between these two extremes. The notch and slur are apparent in the residual signal 535 associated with this model, along with a small signal error at the beginning of the QRS complex.

If the z-transform variable in the z-domain expression is replaced with the unit forward shift operator q (such that $q^{-1} y(n) = y(n-1)$, etc.), parameters A(q) and B(q) that correspond in the frequency domain to the functions A(z) and B(z) may be produced. These parameters may be modelled using an autoregressive model with an exogenous input (ARX). The ARX model describes a system with an input-output relationship that may be expressed as:

$$A(z)y(n) = B(z)u(n) + e(n)$$

where u(n) is the input (in this case an unit impulse, $u(n) = \delta(n)$), y(n) is the output (the DCT of the QRS waveform), and e(n) represents a non-predictable white noise term. The ARX model is advantageous in that it defines a linear regression having parameters that can be estimated analytically. The ARX model can be expressed as:

$$y(n) = -\sum_{i=1}^{na} a_i y(n-i) + \sum_{j=0}^{nb} b_j u(n-j) + e(n)$$

$$= \phi^T(n)\theta + e(n)$$

where $\theta = [a_1, a_2 \ldots a_{na}, b_0, b_1, \ldots b_{nb}]^T$ is the parameters vector and $$\phi(n) = [-y(n-1) \ldots -y(n-na)\ u(n)\ u(n-1) \ldots u(n-nb)]^T$$

is the regression vector. From the DCT of the QRS waveform, y(n), and an impulse input, the predicted signal $\hat{y}(n)$ can be expressed as a linear regression:

$$\hat{y}(n) = \phi^T(n)\theta$$

Considering signals of N samples (n=1,2, ..., N) and a model of order na and nb for A(z) and B(z), respectively, the coefficients of these polynomials may be estimated using the well-known prediction error method, in a way that minimizes the model fitting error ($\epsilon(n) = y(n) - \hat{y}(n)$) in the least square sense, with the loss function:

$$V(\theta) = \sum_{n=p+1}^{N} \epsilon^2(n) = \sum_{n=p+1}^{N} [y(n) - \phi^T(n)\theta]^2$$

where p is the greater value between na and nb. The data of N samples include a pre-windowing of p zeros so that the summation starts at the first sample of the signal. The loss function may be written in a matrix form as:

$$V(\theta) = (y - \Phi\theta)^t(y - \Phi\theta)$$

where $$y = [y(p+1)\ y(p+2) \ldots y(N)]$$

and $\Phi$ is the matrix of regression vectors given by $$\Phi = \begin{bmatrix} \phi^T(p+1) \\ \phi^T(p+2) \\ \vdots \\ \phi^T(N) \end{bmatrix}$$

$$= \begin{bmatrix} -y(p) & \ldots & -y(p-na+1) & u(p+1) & \ldots & u(p-nb+1) \\ -y(p+1) & \ldots & -y(p-na+2) & u(p+2) & \ldots & u(p-nb+2) \\ \vdots & & \vdots & \vdots & & \vdots \\ -y(N+1) & \ldots & -y(N-na) & u(N) & \ldots & u(N-nb) \end{bmatrix}$$

Minimizing the loss function, the parameters may be estimated using the expression:

$$\hat{\theta} = (\Phi^T \Phi)^{-1} \Phi^T y$$

assuming that the matrix $\Phi^T \Phi$ is non-singular.

Referring again to FIG. 5, once the model of the DCT of the reference QRS waveform is produced (step 415), it is converted to the time domain using an inverse DCT (IDCT) (step 420). The IDCT of X(k) may be expressed as:

$$x(n) = \sqrt{\frac{2}{N}} \sum_{k=0}^{N-1} C_k X(k) \cos\left[\frac{(2n+1)k\pi}{2N}\right].$$

Figure 7:
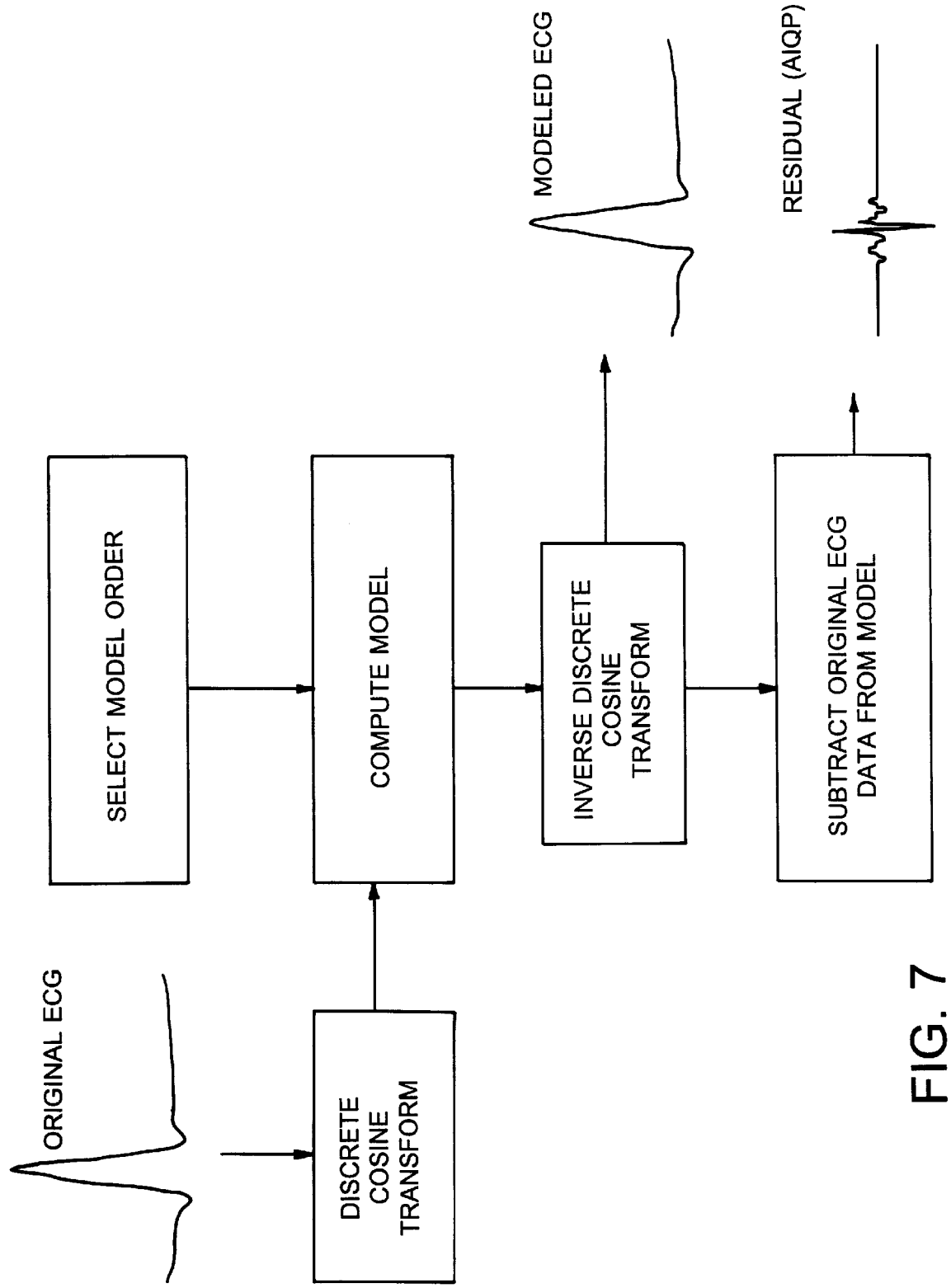
FIG. 7 is a block diagram of a technique for producing an AIQP signal.

This transformed model may then be subtracted from the representative beats for different stages of the stress test to produce the AIQP signals. This procedure is illustrated graphically in FIG. 7.

Another processing approach assumes that AIQP signals change progressively over time during the recording period. An example of when this assumption may apply is when the AIQP signals are monitored during a period of suspected acute myocardial infarction. As an infarction evolves, the AIQP signals change due to changes in ventricular conduction patterns caused by conduction blockage and scar tissue formation. In general, the AIQP signals may be monitored under these conditions by trending values recorded in successive representative beats formed from subensembles obtained during successive recording periods. This approach may use the model of a reference QRS waveform, as described above, or may use a model of the QRS waveform for each beat under consideration.

Referring again to FIG. 2, the AIQP signals may be analyzed by quantifying them and by determining their timing. An AIQP waveform, AIQP(t), can be quantified by calculating its root-mean-squared ("RMS") QRS complex as:

$$AIQP_{rms} = \sqrt{\sum_{t=0}^{T} \|AIQP(t)\|^2 / T} \quad ,$$

Where T is the number of time samples in the QRS complex. The timing, $t_0$, of the AIQP signal can be determined tentatively as the time value corresponding to the weighted center of the AIQP signal such that:

$$\frac{\sum_{t=QRS\ On}^{t_0} \|AIQP(t)\|^2}{\sum_{t=QRS\ On}^{QRS\ Off} \|AIQP(t)\|^2} = 0.5$$

Figure 8:
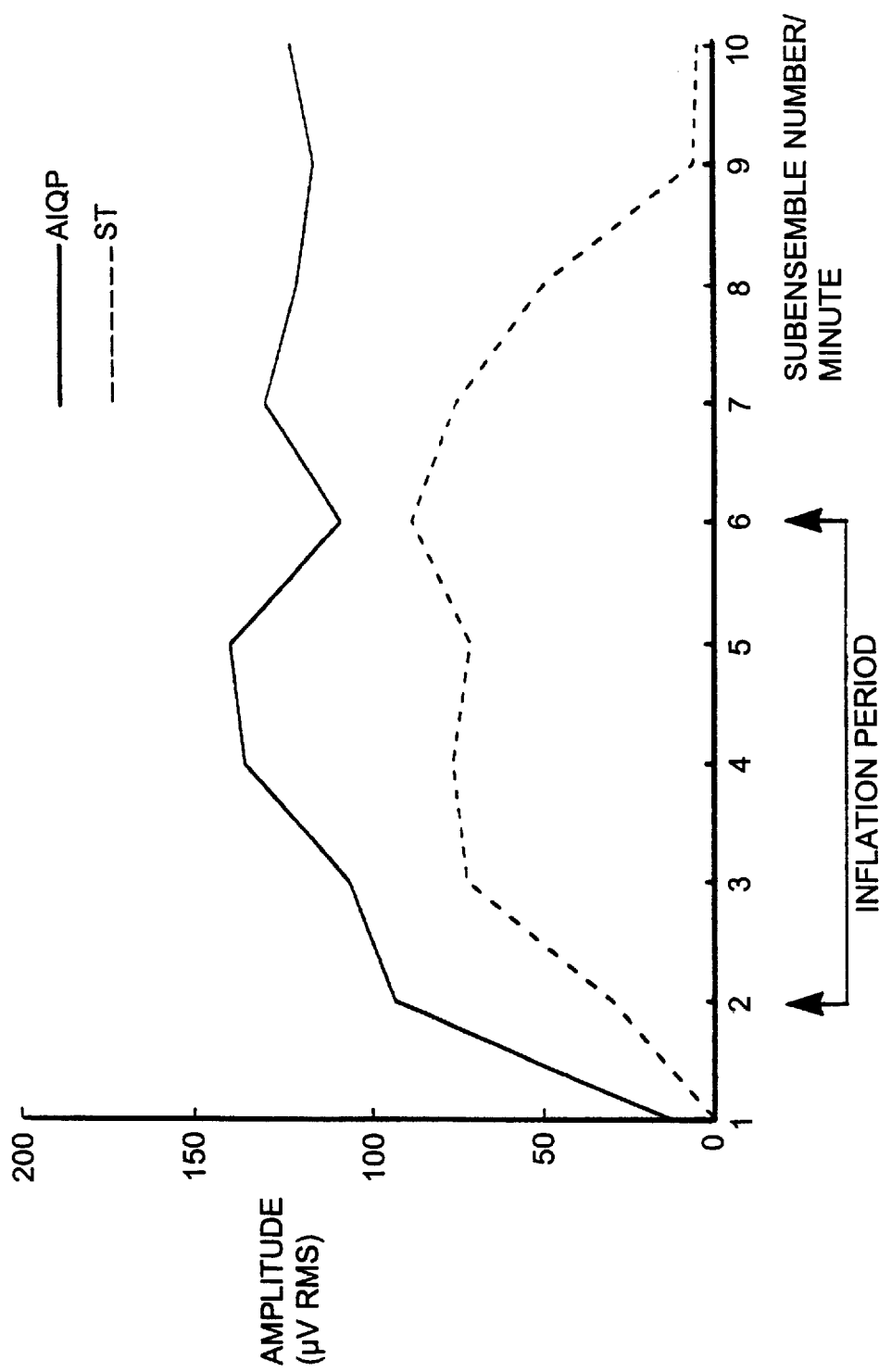
FIG. 8 is a graph of amplitudes of AIQP signals and ST segment variations.
Figure 9:
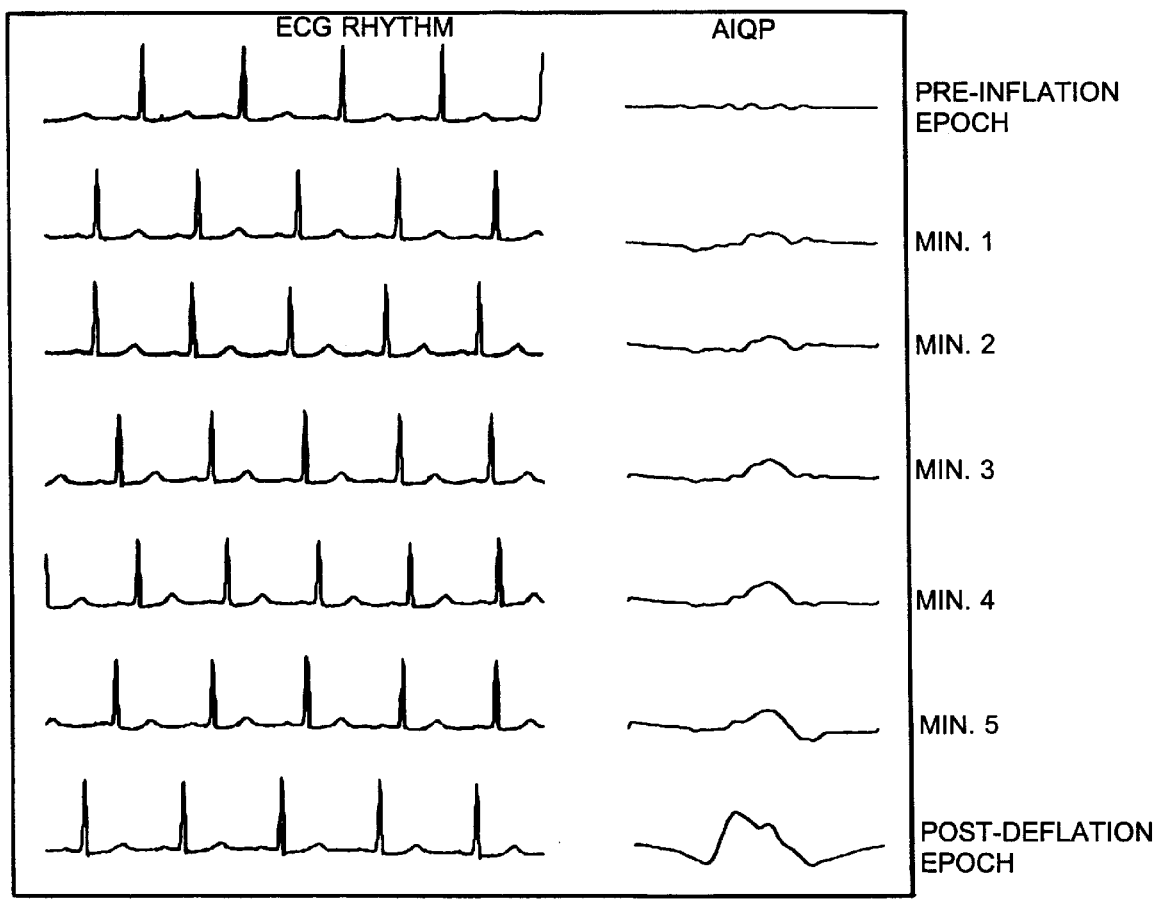
FIG. 9 is a graph of ECG waveforms and AIQP signals.

The RMS and timing values may be determined for each representative beat and analyzed and graphed as a trend. FIG. 8 shows such a trend of $AIQP_{rms}$ values during balloon angioplasty. There is a pre-inflation control period, followed by 5 minutes of balloon inflation, followed by balloon deflation. The AIQP signals have small amplitudes during the pre-inflation period. Their amplitudes rise sharply during balloon inflation and persist in the immediate aftermath of balloon deflation. ECG signals and associated AIQP signals for the angioplasty procedure are shown in FIG. 9. AIQP signals were present in twelve of twelve subjects analyzed. In contrast, ST segment deviation occurred later into the period of balloon inflation and was not always present. Only seven out of twelve subjects studied had clinically significant ST segment deviation.

Figure 10:
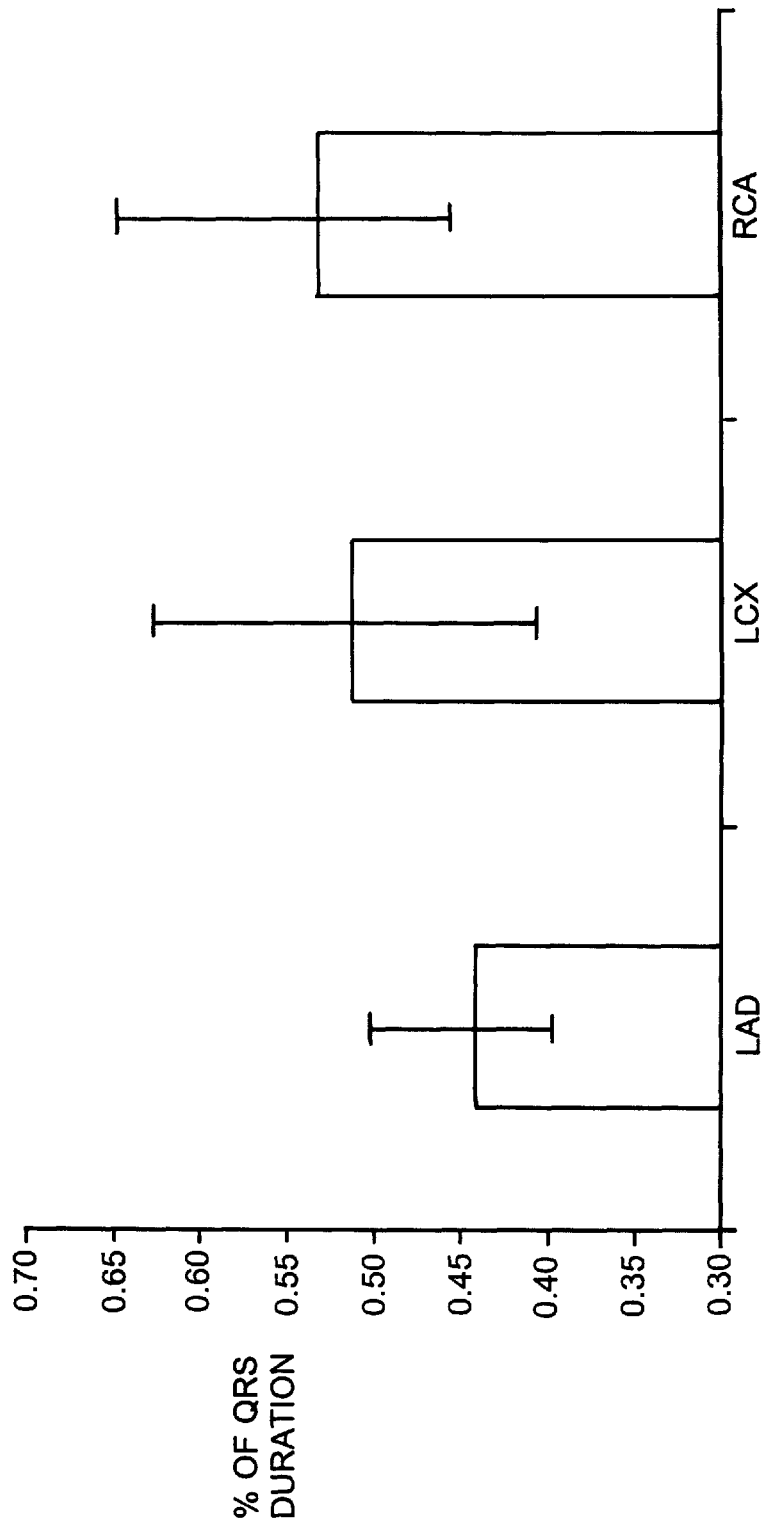
FIG. 10 is a graph showing a relationship between AIQP signal timing and ischemia location.

AIQP timing may be correlated with the arterial location of the balloon. FIG. 10 shows the timing of AIQP signals within the QRS complex for the left anterior descending ("LAD") artery, left circumflex ("LCX") artery, and right coronary artery ("RCA"). As would be expected from anatomy, occlusion of these arteries is associated with disruption of ventricular conduction in the early, mid and late portions of the QRS complex, respectively.

A variety of techniques may be used to reduce noise in the ECG signal and thereby improve the system's ability to detect the AIQP signals. For example, referring to FIG. 11, each electrode 110 may be a multi-segment electrode 1200 that includes a center segment 1205 and four exterior segments 1210a, 1210b, 1210c and 1210d that together surround the center segment 1205. The position of the center segment 1205 corresponds to the average of the positions of the exterior segments 1210a, 1210b, 1210c and 1210d. The diameter of the region defined by the exterior segments is on the order of 2 and 1/8 inches.

The multi-segment electrode 1200 is configured for use with a connector 1215 that is attached to a lead 1220. To this end, the electrode 1200 includes a connection tail 1225. The connection tail 1225 includes five connection holes 1230 for attachment to the connector 1215. Four of the connection holes 1230 are arranged in a square configuration, with a fifth connection hole being located in the center of the square. Each hole 1230 passes through an extension 1235, or trace, of a segment of the electrode 1200. The construction and operation of a connector comparable to the connector 1215 is discussed in detail in U.S. application Ser. No. 08/724,885, entitled "ELECTRODE CONNECTOR" and filed Oct. 3, 1996, which is incorporated by reference.

Figure 12:
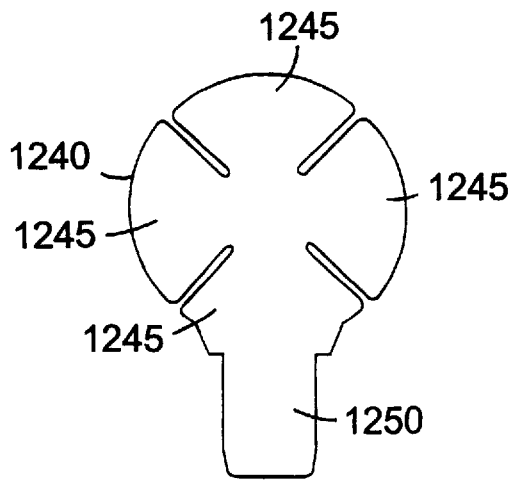
FIGS. 12–15 are bottom views of the electrode of FIG. 11 during different stages of construction of that electrode.

Referring to FIG. 12, the multi-segment electrode 1200 is formed on a basepad 1240. The basepad is made from an insulating, flexible film, such as polyester film. The basepad 1240 is shaped to include a section 1245 corresponding to each segment of the electrode and a section 1250 corresponding to the connection tail 1225.

Figure 13:
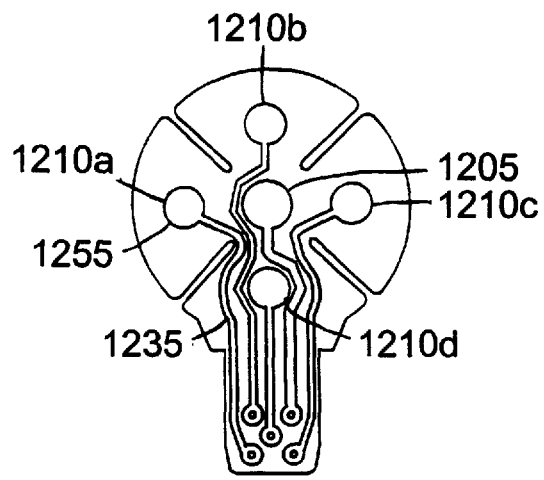
Figure 14:
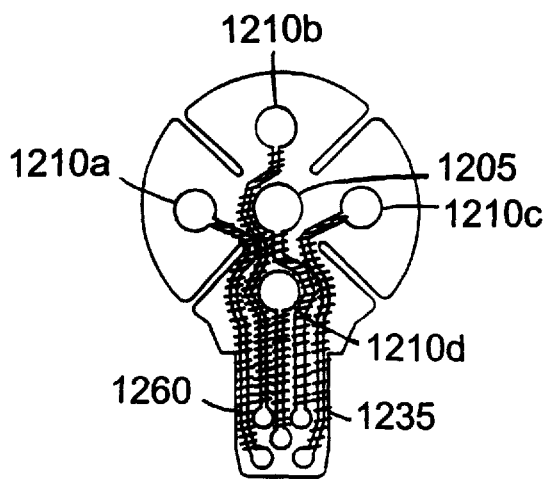

As shown in FIG. 13, the segments 1205, 1210a, 1210b, 1210c and 1210d are formed by printing on the surface of the basepad 1240 with a conductive material 1255, such as silver-chloride ink. The extensions 1235 are formed in the same manner. Next, as shown in FIG. 14, a layer of insulating material 1260 is deposited on the silver-chloride ink 1255 that defines the extensions 1235. With the exception of portions of the extensions that will be adjacent to the holes 1230, the insulating material covers the entire surface area of the extensions.

Figure 15:
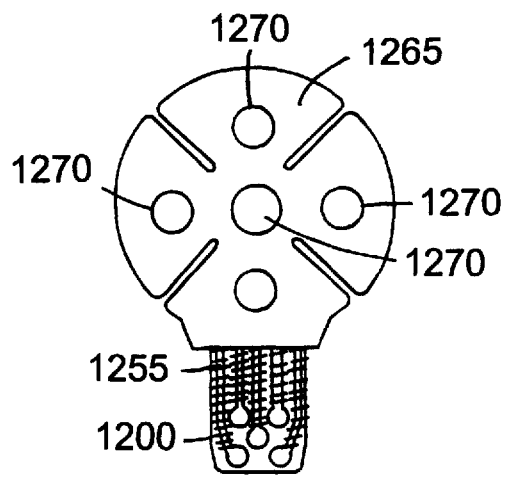
Figure 16:
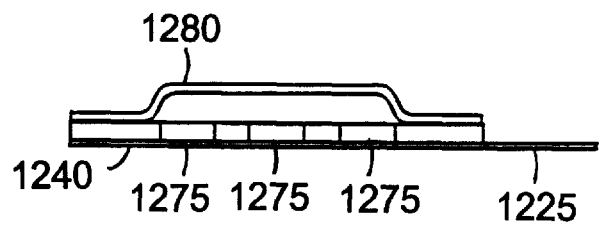
FIG. 16 is a side view of the electrode of FIG. 11.

Referring to FIG. 15, a layer of plastic flexible foam 1265 is attached to the section 1245 of the basepad 1240 corresponding to the segments of the electrode. The foam is positioned on top of the silver-chloride ink 1255 and the insulating material 1260 so that the ink and the insulating material are sandwiched between the foam and the basepad. The foam includes cutout sections 1270 that correspond to the electrode segments 1205, 1210a, 1210b, 1210c and 1210d. The cutout sections form wells that hold electrically conductive gel 1275 (FIG. 16). The gel 1275 provides a conductive path from the patient's skin to the silver-chloride ink that defines each electrode segment.

the holes 1230 are formed through the basepad 1240 and the silver-chloride ink to produce the electrode 1200 illustrated in FIG. 11. Referring to FIG. 16, in storage and prior to use, a cover 1280 is attached to the adhesive surface of the foam 1265 to keep the electrode clean prior to use and to prevent the conductive gel 1275 from drying.

The patient's heart may be stressed using a controlled protocol. The protocol may consist either of exercise or of pharmaceutical stress testing. For example, the patient may be exercised using the treadmill 145. Alternatives to the treadmill, such as climbing and bicycle ergometers, also may be used. In general, the stress protocol will have several stages, including control or warm-up stages, stages featuring progressively heavier stress, a relaxation stage, and a recording stage occurring between fifteen minutes and twenty four hours after the test. Recording of ECG signals may take place during any or all of these stages.

Figure 17:
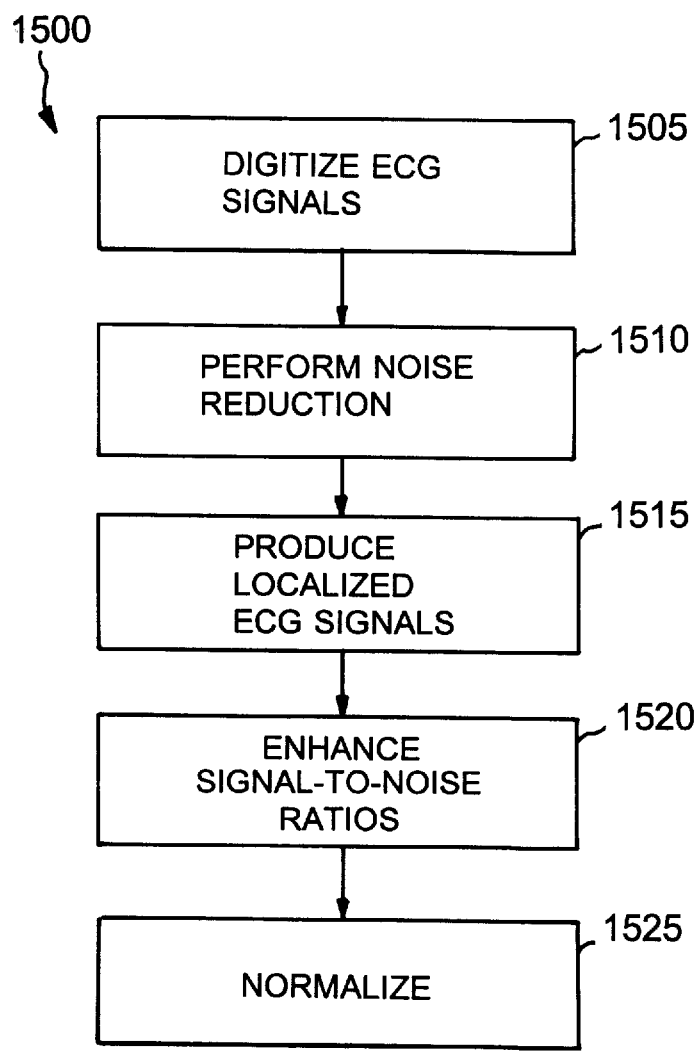
FIG. 17 is a flow chart of a procedure for processing ECG signals.

The processor may generate a set of localized ECG signals. As shown in FIG. 17, the processor may generate the localized ECG signals according to a procedure 1500. Initially, the ECG signals are digitized by the signal conditioning circuitry 125 (step 1505). Digitizing the signals prior to generating the localized ECG signals allows signals from different segments to be weighted in a flexible way, depending on their geometry or location, and permits an impedance measurement, produced from one or more electrodes or electrode segments, to be combined with the ECG signals to remove baseline noise. Localized ECG signals also could be generated by combining analog signals recorded from individual sensing elements of the electrodes or electrode segments prior to digitizing those signals.

Next, noise introduced by, for example, motion artifact, muscular activity or ECG baseline wander, is removed using impedance measures recorded from one or more electrodes and other techniques (step 1510). Techniques for reducing noise in ECG signals are described in U.S. application Ser. No. 08/557,883, entitled "USING RELATED SIGNALS TO REDUCE ECG NOISE" and filed Nov. 14, 1995, which is incorporated by reference.

The localized ECG signals then are produced from the noise-reduced ECG signals (step 1515). Each localized ECG signal corresponds to an approximation of the surface differential signal, also known as the Laplacian signal, which is defined as:

$$\frac{\partial^2 \phi}{\partial x^2} + \frac{\partial^2 \phi}{\partial y^2} = \frac{-4\pi}{\epsilon} \rho_{projected}$$

where $\phi(x,y)$ is the body surface potential, $\rho_{projected}$ is the summed charge density of cardiac sources distant from the surface, and $\epsilon$ is the permittivity of the body considered as a volume conductor. See R. Plonsey, "Laws governing current flow in the volume conductor", in *The Theoretical Basis of Electrocardiogaphy*, C. V. Nelson and D. B. Geselowitz Eds., Clarendon Press, Oxford pp. 165–174, 1976, which is incorporated by reference. For a multi-segment electrode having four exterior segments, the localized ECG signal ($S_L$) is produced as:

$$S_L = S_C - (S_{E1} + S_{E2} + S_{E3} + S_{E4})/4,$$

where $S_C$ is the signal produced by the center segment and $S_{E1}$, $S_{E2}$, $S_{E3}$ and $S_{E4}$ are the signals produced by the exterior segments.

After the localized ECG signals are produced, the signal-to-noise ratios of the signals are enhanced (step 1520). Enhancement of the signal-to-noise ratio includes estimating a representative localized ECG signal during each period of the stress test. A localized ECG signal may be modelled as:

$$x(t) = s(t) + n(t)$$

where $x(t)$ is the ECG signal, $s(t)$ is the cardiac signal component, and $n(t)$ is noise.

In one approach to enhancing the signal-to-noise ratio, a median beat is computed for an ensemble of beats. With reference to the ECG waveform of FIG. 3, the beats of the ensemble are time-aligned by determining fiducial points of the QRS complex of each beat and aligning the beats relative to the fiducial points. For each time increment, corresponding values for the ensemble of beats are ranked according to their magnitudes. The median beat is then computed by selecting the median value for each time increment. A signal-to-noise-ratio-enhanced ECG waveform $x'(t)$ composed of median beats produced in this manner is substituted for the ECG waveform $x(t)$ in subsequent processing.

The median beat may be computed using a moving-average procedure in which the oldest beat is dropped from the ensemble when a new beat is added. This procedure ensures that sudden changes in the ECG waveform resulting from, for example, increases in noise do not distort the median beats that comprise the noise-reduced waveform. The median beats may be further immunized from corruption due to noise by limiting the change in the value of a time sample between median beats to a maximum value, such as, for example, 10 $\mu V$. The median beat computation is useful when the initial signal-to-noise ratio is poor and there are only a small number of beats available for processing.

An alternative approach to enhancing the signal-to-noise ratio is to perform ensemble averaging of the available beats. For an ensemble of I time-aligned beats, the ensemble average, $x'(t)$, is given by:

$$x'(t) = \sum_{i=1}^{I} \frac{x_i(t)}{I} = s(t) + \frac{n'(t)}{\sqrt{I}},$$

where the subscript i refers to the beat number in the ensemble (1 to I), $s(t)$ is the repetitive component of the cardiac signal, and $n'(t)$ is the noise of a typical beat, assuming that the noise is distributed as a Gaussian across the ensemble and is uncorrelated with the cardiac signal. See P. Lander et al., "Principles and Signal Processing Techniques of the High Resolution Electrocardiogram", *Prog. Cardiovasc. Dis.* 35(3):169–188, 1992, which is incorporated by reference. The averaging process attenuates the noise in a statistically predictable fashion, without affecting the cardiac signal component.

Ensemble averaging produces a good unbiased estimate of the cardiac signal component. An enhancement of this approach is to reject beats that are adversely noisy from the ensemble average on the basis of signal variance measurements. See P. Lander et al., "Principles and Signal Processing Techniques of the High Resolution Electrocardiogram", *Prog. Cardiovasc. Dis.* 35(3):169–188, 1992. As also noted in that reference, another enhancement is to apply an a posteriori Wiener filter to the ensemble average to improve the mean-squared error of the cardiac signal estimate.

Next, the localized ECG signals are normalized (step 1525). (Normalization also could be performed before the signal-to-noise ratios of the ECG signals are enhanced.) The normalization step adjusts the scale of the localized ECG signal to obtain a uniform measurement of ST segment deviation that can be related to myocardial ischemia. Normalization is achieved by multiplying the ECG waveform by a normalization, or scaling, function. This results in localized ECG signals that are comparable to each other, either between different locations on the body surface or between different patients.

In a first method of normalization, the localized ECG signals are scaled by the maximum peak-to-peak value of the QRS complex (see FIG. 3) at the center segment of the corresponding multi-segment electrode. Other suitable scale factors include amplitudes recorded from the QRS or T wave or the ECG value anywhere within the ST segment. The scale function also may be derived from a bipolar ECG, multipolar ECG, or the Laplacian ECG itself. An alternative approach is to scale all localized ECG's from one patient with a single value recorded from the set of unipolar, multipolar, or Laplacian ECG's recorded from the body surface of that patient. For example, this value may be the maximum value of the peak-to-peak amplitude of the QRS complex for any electrode segment, or the maximum value of the ST segment of the ECG for any electrode segment.

Other embodiments are within the scope of the following claims.

What is claimed is:

1. A method of detecting abnormal cardiac activity in a patient, the method comprising:

acquiring an electrocardiogram waveform associated with a first level of physiologic activity of the patient and an electrocardiogram waveform associated with a second, different level of physiologic activity of the patient; and comparing QRS complexes of the electrocardiogram waveforms to identify an abnormal portion of the QRS complex of the electrocardiogram waveform associated with the second level of physiologic activity.

2. The method of claim 1, further comprising stressing the patient's heart to produce the second level of physiologic activity.

3. The method of claim 2, wherein:
stressing the patient's heart comprises performing a physiological stress test on the patient, the physiological stress test including an exercise stage and a non-exercise stage,
the first level of physiologic activity is associated with the non-exercise stage of the stress test, and
the second level of physiologic activity is associated with the exercise stage of the stress test.

4. The method of claim 2, wherein stressing the patient's heart comprises using pharmaceutical stress.

5. The method of claim 1, further comprising:
identifying subensembles of beats in the electrocardiogram waveforms corresponding to the first and second levels of physiologic activity; and
processing each subensemble of beats to produce a representative beat;
wherein the step of comparing comprises comparing QRS complexes of the representative beats of the electrocardiogram waveforms to identify an abnormal portion of the QRS complex of the electrocardiogram waveform associated with the second level of physiologic activity.

6. The method of claim 5, wherein the step of processing each subensemble of beats comprises producing a representative beat using subensemble averaging.

7. The method of claim 5, wherein the step of processing each subensemble of beats comprises producing a representative beat by computing a measure of statistical central tendency from the subensemble of beats.

8. The method of claim 1, wherein the step of comparing comprises subtracting a QRS complex of the electrocardiogram associated with the first level of physiologic activity from a QRS complex of the electrocardiogram associated with the second level of physiologic activity and using results of the subtraction in identifying the abnormal portion of the QRS complex of the electrocardiogram waveform associated with the second level of physiologic activity.

9. The method of claim 1, further comprising generating a model of a QRS complex of the electrocardiogram waveform associated with the first level of physiologic activity and using the model in comparing QRS complexes of the electrocardiogram waveforms.

10. The method of claim 9, wherein the step of comparing comprises subtracting the model of the QRS complex of the electrocardiogram associated with the first level of physiologic activity from a QRS complex of the electrocardiogram associated with the second level of physiologic activity and using results of the subtraction in identifying the abnormal portion of the QRS complex of the electrocardiogram waveform associated with the second level of physiologic activity.

11. The method of claim 1, further comprising generating models of QRS complexes of the electrocardiogram waveforms, wherein the step of comparing comprises subtracting from the QRS complex of each electrocardiogram waveform the model of the QRS complex of that waveform and using results of the subtractions in identifying the abnormal portion of the QRS complex of the electrocardiogram waveform associated with the second level of physiologic activity.

12. The method of claim 1, further comprising determining a root-mean-square amplitude of the abnormal portion of the QRS complex and using the determined amplitude to detect further abnormal cardiac activity.

13. The method of claim 1, further comprising determining a duration of the abnormal portion of the QRS complex and using the determined duration to detect further abnormal cardiac activity.

14. The method of claim 1, further comprising measuring an energy of the abnormal portion of the QRS complex and using the measured energy to detect further abnormal cardiac activity.

15. The method of claim 1, further comprising measuring timing of the abnormal portion of the QRS complex relative to the QRS complex and using the measured timing to detect further abnormal cardiac activity.

16. The method of claim 1, further comprising measuring bandwidth of the abnormal portion of the QRS complex relative to the QRS complex and using the measured bandwidth to detect further abnormal cardiac activity.

17. The method of claim 1, further comprising:
acquiring electrocardiogram waveforms associated with other levels of physiologic activity of the patient;
comparing QRS complexes of the electrocardiogram waveforms to identify abnormal portions of the QRS complexes of the electrocardiogram waveform associated with the second level of physiologic activity and the electrocardiogram waveforms associated with other levels of physiologic activity; and
processing the abnormal portions of the QRS complexes to detect further abnormal cardiac activity.

18. The method of claim 17, wherein processing portions of the QRS complexes comprises comparing the abnormal portions of the QRS complexes.

19. The method of claim 17, wherein processing portions of the QRS complexes comprises measuring a parameter of each of the abnormal portions of the QRS complexes and comparing parameters associated with different QRS complexes.

20. The method of claim 17, wherein processing portions of the QRS complexes further comprises identifying a trend in abnormal portions of the QRS complexes for changing levels of physiologic activity.

21. The method of claim 17, further comprising generating models of QRS complexes of the electrocardiogram waveforms, wherein comparing QRS complexes of the electrocardiogram waveforms to identify abnormal portions of the QRS complexes of the electrocardiogram waveform associated with the second level of physiologic activity and the electrocardiogram waveforms associated with other levels of physiologic activity comprises subtracting from the QRS complex of each electrocardiogram waveform the model of the QRS complex of that waveform and using results of the subtractions in identifying the abnormal portion of the QRS complex of the electrocardiogram waveform associated with the second level of physiologic activity.

22. The method of claim 1, further comprising detecting myocardial ischemia by analyzing the abnormal portion of the QRS complex.

23. The method of claim 22, further comprising determining a quantitative measure of a degree of myocardial ischemia by analyzing the abnormal portion of the QRS complex.

24. The method of claim 22, further comprising determining a location of the myocardial ischemia by analyzing the abnormal portion of the QRS complex.

25. A system for detecting abnormal cardiac activity in a patient, the system comprising:
means for acquiring an electrocardiogram waveform associated with a first level of physiologic activity of the patient and an electrocardiogram waveform associated with a second, different level of physiologic activity of the patient;
means for comparing QRS complexes of the electrocardiogram waveforms to identify an abnormal portion of the QRS complex of the electrocardiogram.

26. The system of claim 25, further comprising means for stressing the patient's heart to produce the second level of physiologic activity.

27. The system of claim 26, wherein:
the means for stressing the patient's heart comprises means for performing a physiological stress test on the patient, the physiological stress test including an exercise stage and a non-exercise stage,
the first level of physiologic activity is associated with the non-exercise stage of the stress test, and
the second level of physiologic activity is associated with the exercise stage of the stress test.

28. The system of claim 26, further comprising means for generating a model of a QRS complex of the electrocardiogram waveform associated with the first level of physiologic activity, wherein the means for comparing uses the model in comparing QRS complexes of the electrocardiogram waveforms.

29. The system of claim 28, wherein the means for comparing comprises means for subtracting the model of the QRS complex of the electrocardiogram associated with the first level of physiologic activity from a QRS complex of the electrocardiogram associated with the second level of physiologic activity and using results of the subtraction in identifying the abnormal portion of the QRS complex of the electrocardiogram waveform associated with the second level of physiologic activity.

30. The system of claim 26, wherein the means for stressing the patient's heart comprises means for using pharmaceutical stress.

31. The system of claim 25, further comprising:
means for identifying subensembles of beats in the electrocardiogram waveforms corresponding to the first and second levels of physiologic activity; and
means for processing each subensemble of beats to produce a representative beat;
wherein the means for comparing comprises means for comparing QRS complexes of the representative beats of the electrocardiogram waveforms to identify an abnormal portion of the QRS complex of the electrocardiogram waveform associated with the second level of physiologic activity.

32. The system of claim 31, wherein the means for processing each subensemble of beats comprises means for producing a representative beat using subensemble averaging.

33. The system of claim 31, wherein the means for processing each subensemble of beats comprises means for producing a representative beat by computing a measure of statistical central tendency from the subensemble of beats.

34. The system of claim 25, wherein the means for comparing comprises means for subtracting a QRS complex of the electrocardiogram associated with the first level of physiologic activity from a QRS complex of the electrocardiogram associated with the second level of physiologic activity and using results of the subtraction in identifying the abnormal portion of the QRS complex of the electrocardiogram waveform associated with the second level of physiologic activity.

35. The system of claim 25, further comprising means for generating models of QRS complexes of the electrocardiogram waveforms, wherein the means for comparing comprises means for subtracting from the QRS complex of each electrocardiogram waveform the model of the QRS complex of that waveform and using results of the subtractions in identifying the abnormal portion of the QRS complex of the electrocardiogram waveform associated with the second level of physiologic activity.

36. The system of claim 25, further comprising means for determining a root-mean-square amplitude of the abnormal portion of the QRS complex and using the determined amplitude to detect further abnormal cardiac activity.

37. The system of claim 25, further comprising means for determining a duration of the abnormal portion of the QRS complex and using the determined duration to detect further abnormal cardiac activity.

38. The system of claim 25, further comprising means for measuring an energy of the abnormal portion of the QRS complex and using the measured energy to detect further abnormal cardiac activity.

39. The system of claim 25, further comprising means for measuring timing of the abnormal portion of the QRS complex relative to the QRS complex and using the measured timing to detect further abnormal cardiac activity.

40. The system of claim 25, further comprising means for measuring bandwidth of the abnormal portion of the QRS complex relative to the QRS complex and using the measured bandwidth to detect further abnormal cardiac activity.

41. The system of claim 25, further comprising:
means for acquiring electrocardiogram waveforms associated with other levels of physiologic activity of the patient;
means for comparing QRS complexes of the electrocardiogram waveforms to identify abnormal portions of the QRS complexes of the electrocardiogram waveform associated with the second level of physiologic activity and the electrocardiogram waveforms associated with other levels of physiologic activity; and
means for processing the abnormal portions of the QRS complexes to detect further abnormal cardiac activity.

42. The system of claim 41, wherein the means for processing comprises means for comparing the abnormal portions of the QRS complexes.

43. The system of claim 41, wherein the means for processing comprises means for measuring a parameter of each of the abnormal portions of the QRS complexes and comparing parameters associated with different QRS complexes.

44. The system of claim 41, wherein the means for processing further comprises means for identifying a trend in abnormal portions of the QRS complexes for changing levels of physiologic activity.

45. The system of claim 41, further comprising means for generating models of QRS complexes of the electrocardiogram waveforms, wherein the means for comparing comprises means for subtracting from the QRS complex of each electrocardiogram waveform the model of the QRS complex of that waveform and using results of the subtractions in identifying the abnormal portion of the QRS complex of the electrocardiogram waveform associated with the second level of physiologic activity.

46. The system of claim 25, further comprising means for detecting myocardial ischemia by analyzing the abnormal portion of the QRS complex.

47. The system of claim 46, further comprising means for determining a quantitative measure of a degree of myocardial ischemia by analyzing the abnormal portion of the QRS complex.

48. The system of claim 46, further comprising means for determining a location of the myocardial ischemia by analyzing the abnormal portion of the QRS complex.

* * * * *